United States Patent [19]

Chen et al.

[11] Patent Number: 5,382,580

[45] Date of Patent: Jan. 17, 1995

[54] N9 MORPHOLINO DERIVATIVES OF 7,8-DISUBSTITUTED GUANINES

[75] Inventors: Robert Chen, Belle Mead, N.J.; Michael G. Goodman, Rancho Sante Fe, Calif.; Allen Reitz, Lansdale, Pa.

[73] Assignee: The Scripps Research Institute, La Jolla, Calif.

[21] Appl. No.: 250,484

[22] Filed: May 27, 1994

[51] Int. Cl.$^6$ .................. A61K 31/535; C07D 473/18
[52] U.S. Cl. .................. 514/234.2; 544/118
[58] Field of Search ........ 544/118; 514/234.2

[56]   References Cited
   U.S. PATENT DOCUMENTS 3,532,695 10/1970 Dvonch et al. .................. 544/118
   5,011,828  4/1991 Goodman et al. ................. 514/45
   5,093,318  3/1992 Goodman et al. ................. 514/45

Primary Examiner—Robert W. Ramsuer
Attorney, Agent, or Firm—Welsh & Katz, Ltd.

[57] ABSTRACT

Immunostimulating 7,8-disubstituted guanine derivatives that also contain a morpholinyl group as a position-9 substituent are disclosed whose structures are represented by formula I

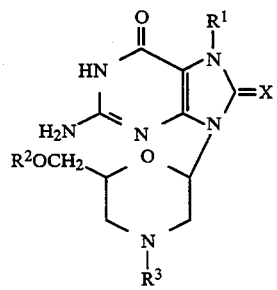

wherein X is O or S; $R^1$ is a hydrocarbyl or substituted hydrocarbyl group having a length of about one to about seven carbon atoms; $R^2$ is a hydrogen or $C_1$–$C_8$ acyl; $R^3$ is hydrogen, a $C_1$–$C_5$ aliphatic hydrocarbyl, aralkyl or substituted aralkyl group; and the pharmaceutically acceptable base addition salts thereof. Also disclosed are compositions containing an immunostimulating substituted guanine derivative and processes for using the same.

11 Claims, No Drawings

N9 MORPHOLINO DERIVATIVES OF 7,8-DISUBSTITUTED GUANINES

This invention was made with government support under Contract No. AI 15284 awarded by the National Institutes of Health. The government has certain rights in the invention.

DESCRIPTION

TECHNICAL FIELD

The present invention relates to immunostimulating compounds, and more specifically to 7,8-disubstituted guanine derivatives that also contain a 9-morpholino substituent, as well as to compositions containing those derivatives and processes for their use.

BACKGROUND OF THE INVENTION

An animal's immune system is comprised of numerous elements that counteract, eliminate, or neutralize agents that are recognized by that system as foreign to the animal host. Generally, but not necessarily, the agent or substance recognized as foreign by the immune system has its origin exogenous to the animal host. Exemplary of such exogenous substances are infectious bacteria and the by-products of their cellular activity, virus particles and their proteins, proteins injected by insect stings, and the like. In autoimmune diseases, such as rheumatoid arthritis, the host animal's immune system perceives host-made proteins (self-made proteins) as if they were foreign.

The principal effectors of the immune system are the B and T leukocytes. The B lymphocytes mediate humoral immunity, whereas cytotoxic T cells, natural killer (NK) cells, and T cell mediators of delayed-type hypersensitivity are principal effectors of cell-mediated immunity.

T cells express important surface antigens designated CD 2, 3, 4, 5 and 8 that are related to T cell functions. Helper T cell precursors are of the CD 4+,8−, phenotype. Th$_1$ and Th$_2$ subsets of CD 4+, 8− T cells normally participate in the activation and regulation of B cells. These helper T cells are known to assist in activation, differentiation and regulation of immunoglobulin-secreting B cells after antigen presenting cells, such as B cells, macrophages and dendritic cells, take up, process, and present antigen in association with class II MHC molecules. The Th$_2$ cells provide cell associated and soluble (LK) signals for B cell proliferation and differentiation, including interleukins (IL)-4, 5, 6 and 10. Th$_1$ cells secrete a different spectrum of regulatory cytokines, including IL-2 and interferon (IFN)-$\gamma$.

Guanosine-3', 5'-cyclic monophosphate (cGMP) was previously thought to be implicated as a naturally occurring agent for providing the required intracellular second message for B cell proliferation. 8-Bromoguanosine-3', 5'-cyclic guanosine monophosphate (8-Br-cGMP, an analog of cGMP,) has been found to be a weak synthetic intracellular B lymphocyte mitogen.

The immune response can be modified by artificial suppression (herein called immunosuppression) or enhancement (immunopotentiation, immunostimulation or immuno-enhancement). Immunosuppression; i.e., naturally or artificially induced decreased responsiveness, can be achieved by eight general methods: (1) administration of an appropriate form or amount of antigen, (2) administration of specific antisera or antibody, (3) use of other biologic reagents such as antilymphocyte antisera, (4) use of immuno-suppressive drugs or hormones, (5) radiation, and (6) surgical removal of lymphoid tissue, (7) aging (or senescence) or certain heritable conditions, and (8) infection with certain microbial agents. Immunopotentiation can be achieved by administration of an agent effecting an increase in the rate at which the immune response develops, an increase in the intensity or level of the response, a prolongation of the response, or the development of a response to an otherwise non-immunogenic substance.

The agents that are known to enhance immune responses are generally termed adjuvants. Based upon relative activities, adjuvants can be placed into one of two general categories: (1) those providing general potentiation; i.e., substances that enhance both cellular and humoral immune responses for a wide variety of antigens, and (2) those providing specific potentiation; i.e., substances that enhance specific responses to certain antigens only. Exemplary adjuvants include the following categories: (1) water and oil emulsions, e.g., Freund's adjuvant, (2) synthetic polynucleotides, (3) hormones, drugs and cyclic nucleotides, (4) endotoxins, (5) proteinaceous lymphokines and monokines such as the interleukins and growth factors.

An example of a substance capable of specifically potentiating the immune response is a transfer factor, a dialyzable leukocyte extract (DLE) obtained from human peripheral leukocytes. It has been reported that the transfer factor exhibits some effectiveness in patients with immunodeficiencies and possible effectiveness in cancer patients and in patients with limited immunodeficiencies. However, much remains to be learned about this particular substance.

In some diseases and physiological conditions such as X-linked agammaglobulinemias, senescence and drug-induced-immunosuppression, B cell activation and differentiation is lacking and/or exists only at a reduced level, thereby lessening the immune response of the host. These diseases and conditions are representative of naturally and artificially induced immunosuppressed states. Here, enhanced activation and differentiation, if it can be effected, tends to beneficially lessen the disease manifestation and/or improve the patient's condition.

An immunopotentiated state can be illustrated by the bodily condition after vaccination. Here, the immune response, already enhanced due to antigenic stimulation could be beneficially enhanced still further to provide an improved degree and/or duration of immunity by either a subsequent exposure to antigen, use of an adjuvant, or both.

U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-1 like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, whereas electron donating substituents such as an amino group were found to be inactive.

U.S. Pat. No. 4,643,992 further discloses the use of derivatives of 8-hydroxyguanine (8-oxoguanine), 7-methyl-8-oxoguanine and 7-methyl-8-thioxoguanine in modulating animal cellular responses. Further results using guanine derivatives disclosed in U.S. Pat. No. 4,539,205 are also disclosed in U.S. Pat. No. 4,643,992, as are similar results using guanine derivatives disclosed for the first time in that patent.

Still further, several papers and book chapters have been published by some of the present inventors and their co-workers relating to still further effects of compounds disclosed and claimed in U.S. Pat. No. 4,643,992. Exemplary of those published papers are Goodman, *Proc. Soc. Exp. Biol. Med.*, 179:479 (1985); Goodman, *J. Immunol.*, 136:3335 (1986); Goodman and Weigle in *Purine Metabolism In Man, Part 3*, Nyhan and Thompson, eds., Plenum Press, New York, page 451 and 443 (1986); Goodman and Weigle, *J. Immunol.*, 135:3284 (1985); Goodman and Wolferr, *Immunol. Res.*, 5:71 (1986); Goodman, *J. Immunol*, 137:3753 (1986); and Goodman and Hennen, *Cell. Immunol.*, 102:395 (1986).

U.S. Pat. No. 5,011,828 describes certain 7,8-disubstituted guanine nucleosides that enhance an immune response in human and animal cells. The nucleosides described in this patent are improvements over the other substituted guanine derivatives mentioned previously in that they either provide a similar response at a lower dose or provide a greater enhancement of the response at a given dose. The 7-substituents of these substituted guanine derivatives are straight, cyclic or branched chain hydrocarbyl radicals having a length greater than an ethyl group and less than a decyl group.

U.S. Pat. No. 5,093,318 describes further 7,8-disubstituted guanine nucleosides that are also immunostimulators. Those immunostimulators had similar 8-substituents to the compounds of No. 5,011,828, but had heteroatom-containing substituents at the 7-position instead of hydrocarbyl substituents.

The disclosure that follows describes 7,8-disubstituted guanine derivatives whose 9-substituent groups are not saccharide derivatives as were the 1-ribosyl derivatives of either of U.S. Pat. No. 5,093,318 or U.S. Pat. No. 5,011,828.

SUMMARY OF THE INVENTION

It has been found that N-9 morpholino derivatives of 7,8-disubstituted guanines have immunoenhancing (immunostimulatory) properties. A contemplated compound corresponds in structure to the following general formula I:

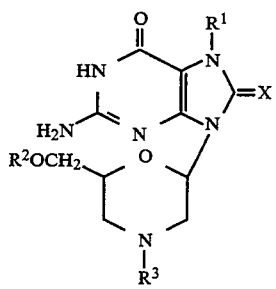

wherein X is O or S, most preferably O;

$R^1$ is a hydrocarbyl or substituted hydrocarbyl group (moiety or radical) having a length of one to about seven carbon atoms. More preferably, $R^1$ is selected from the group consisting of (i) a $C_1$–$C_5$ aliphatic hydrocarbyl group, (ii) an aralkyl hydrocarbyl radical such as a benzyl or phenethyl radical and (iii) a substituted aralkyl radical whose substituent is selected from the group consisting of halogen, nitro, $C_1$–$C_2$ alkyl, trifluoromethyl, amino and substituted amino, wherein the amine substituents are mono- or di-$C_1$–$C_2$ alkyl, $C_1$–$C_3$ acyl and sulfonyl groups;

$R^2$ is hydrogen or a $C_1$–$C_8$ acyl radical;

$R^3$ is selected from the group consisting of a hydrogen, a $C_1$–$C_5$ aliphatic hydrocarbyl, an aralkyl and a substituted aralkyl group; and the pharmaceutically acceptable base addition salts thereof.

Pharmaceutical compositions containing such compounds and methods of enhancing immune response in human and animal cells using such compounds are also disclosed.

DETAILED DESCRIPTION OF THE INVENTION

A. Compounds

More particularly, a compound of the present invention is represented by the general formula I:

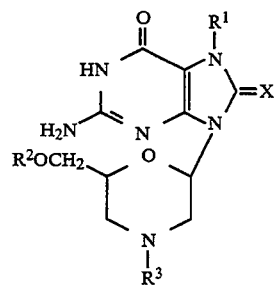

wherein X is O or S, most preferably O;

$R^1$ is a hydrocarbyl or substituted hydrocarbyl group (moiety or radical) having a length of one to about seven carbon atoms. More preferably, $R^1$ is selected from the group consisting of (i) a $C_1$–$C_5$ aliphatic hydrocarbyl group, (ii) an aralkyl hydrocarbyl radical such as a benzyl or phenethyl radical and (iii) a substituted aralkyl radical whose substituent is selected from the group consisting of halogen, nitro, $C_1$–$C_2$ alkyl, trifluoromethyl, amino and substituted amino, wherein the amine substituents are mono- or di-$C_1$–$C_2$ alkyl, $C_1$–$C_3$ acyl and sulfonyl groups; and $R^2$ is hydrogen or a $C_1$–$C_8$ acyl radical;

$R^3$ is selected from the group consisting of hydrogen, $C_1$–$C_5$ aliphatic hydrocarbyl, aralkyl and substituted aralkyl groups; and the pharmaceutically acceptable base addition salts thereof.

The hydrocarbyl radical chain lengths are measured along the longest linear carbon chain in the molecule. Such lengths can be readily determined by using published bond angles, bond lengths and atomic radii, as needed, to draw and measure a staggered chain, by building models using commercially available kits whose bond angles, lengths and atomic radii are in accord with accepted, published values, or by use of well known computer programs. Radical lengths can also be determined somewhat less exactly by assuming unsaturated bonds to have the same length as saturated bonds and that bond angles for unsaturated bonds are the same as those for saturated bonds, although the above mentioned modes of measurement are preferred. Where a heteroatom is present, that atom is considered to be a carbon atom for purposes of measuring substituent chain length. For example, a 4-nitrobenzyl substituent group is considered to have a length of about seven carbon atoms.

Hydrocarbons and hydrocarbyl radicals contain only carbon and hydrogen atoms. Hydrocarbyl radicals useful as $R^1$ groups can broadly be divided into aliphatic and aromatic radicals. Aliphatic radicals include (i) saturated alkane (alkyl radicals) and (ii) mono- and polyunsaturated alkenes and alkynes (alkenyl and alkynyl radicals), respectively. Cyclic, straight chain and branched chain radicals exist for each type of aliphatic radical. Contemplated aromatic $R^1$ aralkyl radicals include aralkane, aralkene and aralkyne radicals that contain an aromatic ring linked to an aliphatic group. Aromatic $R^1$ groups are benzyl, phenethyl or benzhydryl groups and their derivatives. Exemplary $R^1$ hydrocarbyl radicals are described below.

As used herein unless otherwise noted, an alkyl substituent group includes straight and branched chains such as methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, hexyl and heptyl, as well as cyclic groups as are discussed hereinafter. Of course, if the alkyl substituent is branched there must be at least 3 carbons. The group of $R^1$ $C_3$–$C_5$ alkyl radicals is more preferred.

Unsaturated radicals constitute yet another group of aliphatic radicals. Exemplary radicals include allyl, 3-butenyl, 2-methyl-3-butenyl and butadienyl. $C_3$–$C_5$ Beta-alkenyl radicals are a particularly preferred group of unsaturated hydrocarbyl radicals. $C_3$–$C_5$ Beta-alkenyl radicals are a particularly preferred group of unsaturated hydrocarbyl radicals. $C_3$–$C_5$ Beta-alkenyl radicals contain an ethylenic double bond beta to the 7-nitrogen atom of the guanosine. Exemplary radicals include allyl (2-propenyl), 2-butenyl, 2-pentyl and 3-methyl-2-butenyl. Allyl is the most preferred $R^1$ group.

Cyclic aliphatic groups include those compounds having 5–7 carbon atoms in the cyclic ring. Exemplary groups include cyclopentyl, cyclohexyl, cycloheptyl, 3-methylcyclopentyl, 4-methylcyclohexyl, and the like. Monoethylenically unsaturated cyclic aliphatic groups are also contemplated such as cyclopent-2-enyl and cyclohex-2-enyl groups.

Aralkyl radicals constitute another group of hydrocarbyl, $R^1$, radicals. Those radicals contain an aromatic ring, and include benzyl, phenethyl and diphenylmethyl (benzhydryl). Benzyl is a particularly preferred $R^1$ radical.

An above-discussed aralkyl hydrocarbyl group or radical can also be substituted by one or more atoms other than carbon and hydrogen. Such a substituted radical is referred to herein as a heteroatom-substituted aralkyl hydrocarbyl group or radical.

Substituted aralkyl radicals are also contemplated $R^1$ radicals. Contemplated aralkyl radicals (benzyl, phenethyl and benzhydryl radicals) can be substituted on their phenyl rings with one or two, preferably one, $C_1$–$C_2$ alkyl or heteroatom-substituents selected from the group consisting of nitro, halogen, trifluoromethyl, amino and substituted amino wherein the amine substituents are mono- or di-$C_1$–$C_2$ alkyl and mono-$C_1$–$C_3$ acyl.

Substituents on a benzyl, phenethyl or benzhydryl group that are electron withdrawing groups relative to hydrogen by resonance or inductive effect as are discussed in Hine, *Physical Organic Chemistry*, 2nd ed., McGraw-Hill Book Co., New York, pages 85–93 (1962) such as cyano, nitro and halogen are preferred. A 4-nitrobenzyl radical is a particularly preferred radical.

Exemplary heteroatom-substituted aralkyl groups include 3- and 4-halo (fluoro, chloro, bromo and iodo) benzyl and phenethyl groups, 3,4-dihalobenzyl such as a 3,4-dichlorobenzyl group, 3- and 4-nitrobenzyl and phenethyl groups, 3- or 4-trifluoromethylbenzyl groups, 2-, 3- or 4-aminobenzyl or phenethyl groups, and their N-formyl or N-acetyl ($C_1$–$C_2$ acyl), or mono- and dimethyl or mono- and diethyl derivatives. Exemplary $C_1$–$C_2$ alkyl-substituted aralkyl groups include 2-, 3- or 4-methylbenzyl or phenethyl groups, a 3,4-dimethylbenzyl group. Aralkyl groups substituted at the 3- or 4-position of the phenyl ring are preferred. Di-$C_1$–$C_2$ alkyl- or $C_1$–$C_3$ acyl-amino-substituted aralkyl groups are preferred over those having one or no substituent on the amine nitrogen atom. A heteroatom-substituted benzyl group is a preferred substituted aralkyl group.

When $R^2$ is hydrogen, the hydroxymethyl of the morpholino group is unsubstituted. That unsubstituted ring can also be named as a 6-(hydroxymethyl)morpholin-2-yl group, radical or moiety. The 2-morpholinyl substituent hydroxymethyl group can also be acylated (esterified) with a $C_1$–$C_8$ acyl moiety, group or radical. Exemplary $C_1$–$C_8$ acyl groups include formyl, acetyl, propionyl, iso-butyryl, hexanoyl, octanoyl, cyclohexylcarbonyl, benzoyl, and toluoyl (toluyl).

A contemplated $C_1$–$C_8$ acyl group can be added to the formed 6-(hydroxymethyl)morpholin-2-yl substituent after the formation of a compound of formula I in which $R^2$ is hydrogen by a well known esterification reaction. Thus, a $C_1$–$C_8$ acyl anhydride such as acetic anhydride or a $C_1$–$C_8$ acyl halide such as benzoyl chloride can be used as the acylating agent in an aprotic standard solvent such as pyridine.

An $R^3$ group of a compound of formula I can be hydrogen, a $C_1$–$C_5$ aliphatic hydrocarbyl group, an aralkyl group or a substituted aralkyl group.

A contemplated $R^3$ $C_1$–$C_5$ aliphatic substituent group includes straight and branched chained moieties. These substituents are exemplified in the prior discussion regarding similar $R^1$ groups.

A contemplated $R^3$ aralkyl group can be a benzyl, phenethyl or diphenylmethyl (benzhydryl) group, as was the case for an $R^1$ substituent. An aralkyl $R^3$ group can also be substituted with a $C_1$–$C_2$ alkyl group or a heteroatom-substituent selected from the group consisting of nitro, halogen, trifluoromethyl, amino and substituted amino wherein the amine substituents are mono- or di-$C_1$–$C_2$ alkyl and mono-$C_1$–$C_2$ acyl. Exemplary substituent $R^3$ aralkyl groups are also as discussed for $R^1$.

A particularly preferred guanine derivative thus contains an X group that is oxygen, O, a most preferred $R^1$ allyl group and one of the above-described $R^2$ and $R^3$ groups, and has a structure represented by formula II, below.

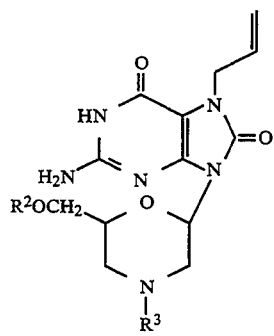

II

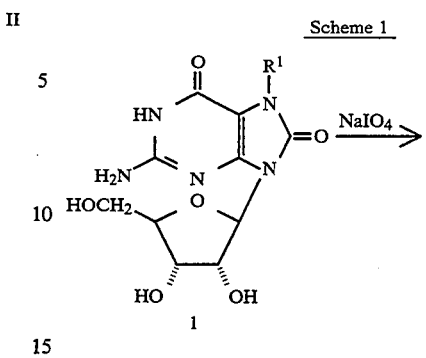

Scheme 1

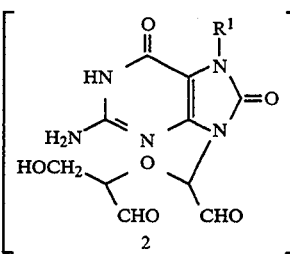

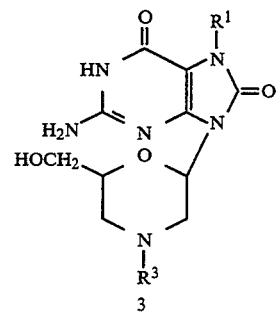

A contemplated guanosine is substantially free from ionic charge at physiological pH values; i.e., about pH 7.0 to about pH 7.5, except for the ionic charges that might be provided by the relatively acidic 1-position ring nitrogen atom. Thus, a useful molecule is free of acid and base-containing moieties that are not present in guanosine such as phosphate, carboxylate or sulfonate moieties and alkylamines. Freedom from ionic charge can be assayed by a lack of relative movement at pH 7.0–7.5 in an electrophoretic study. An amine substituent whose $pK_a$ value is about 6.0 or less can be present as where an $R^1$ group is an aniline derivative. Substantially all carboxylate, phosphate, sulfate or sulfonate substituents bear an ionic charge at physiological pH values.

Many contemplated guanines are themselves weak acids, and as such can form base addition salts. Such salts are useful in providing storage stability and do not provide an added ionic charge to a guanine derivative used in a method of the invention because of the buffering effect provided by the host's blood and lymph systems or the buffer of a culture medium.

Pharmaceutically acceptable, non-toxic base addition salts of guanine derivatives are useful herein, and can be formed by treatment of the immune response-enhancing agent with an appropriate base, in a suitable solvent such as water or a lower alkyl alcohol such as methanol or ethanol. Exemplary inorganic bases include sodium hydroxide, potassium hydroxide, ammonium hydroxide and the like. Exemplary organic bases include tris-(hydroxymethyl)-aminomethane (TRIS), 4-(2-hydroxyethyl)-1-piperazine-ethanesulfonic acid (HEPES) and the like. Conversely, the base addition salt form can be converted to the free guanosine form by treatment with acid.

A contemplated compound can be synthesized by many well known methods. Most preferably, a contemplated compound is prepared from a corresponding substituted guanine derivative such as Compound 1, whose syntheses are disclosed in U.S. Pat. Nos. 5,011,820 and 5,093,318 and the disclosure of Come et al., *Tetrahedron Lett.*, 32:4823–4826 (1991) following the reaction set out in Scheme 1, below, that illustrates synthesis of Compound 3.

As shown, the reaction comprises reacting a 7,8-disubstituted guanosine, Compound 1, (7-allyl-8-oxoguanosine; loxoribine), with sodium periodate, which cleaves the sugar ring as drawn to give dialdehyde Compound 2. This reaction is carried out in water as solvent, and dialdehyde Compound 2 is not isolated, but rather converted on directly to morpholinyl Compound 3 by reductive amination. This latter reductive amination is carried out with a suitable amine ($R^3NH_2$) or ammonia, after adjusting the pH value to 6–7, by the agency of sodium cyanoborohydride. This reaction is typically complete after a time period of about one hour at room temperature. The product is purified by standard chromatographic techniques.

Exemplary compounds of formula I preparable from the compounds of the above U.S. patents are shown in Table 1, below, where $R^2$ and $R^3$ are as before described.

TABLE 1

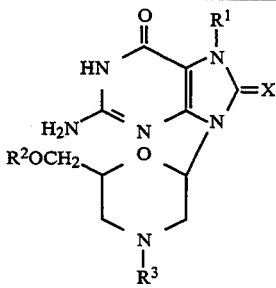

| R¹ | U.S. Pat. No. | Example |
|---|---|---|
| Ethyl | 5,011,828 | 6 |
| Propyl | 5,011,828 | 5 |
| Allyl | 5,011,828 | 8,9 |
| Butyl | 5,011,828 | 2 |
| 2-Butenyl | 5,011,828 | 3 |
| Benzyl | 5,011,828 | 23 |
| Hexyl | 5,011,828 | 4 |
| Carbethoxymethyl | 5,093,318 | 2 |
| 2,3-Dihydroxypropyl | 5,093,318 | 13 |
| 4-Nitrobenzyl | 5,093,318 | 16 |
| 2-Chloroethyl | 5,093,318 | 18 |

B. Compositions

A contemplated composition comprises a diluent amount of a physiologically tolerable carrier (also referred to herein as a vehicle or diluent) admixed with an immunopotentiating (immune response-enhancing or immunostimulating) effective amount of a substituted guanine nucleoside derivative or salt described before.

A composition for in vivo administration is typically provided for per oral or parenteral administration in customary unit dosage compositions. The term "unit dosage" and its grammatical equivalents as used herein refer to physically discrete units suitable as unitary dosages for human patients and other mammals, each unit containing a predetermined effective amount of the substituted guanine derivative active ingredient calculated to produce the desired therapeutic effect in association with the required physiologically tolerable carrier, e.g. a diluent or a vehicle. The specifications for the unit dosage forms of this invention are dictated by and are directly dependent on (a) the unique characteristics of the active substituted guanine derivative ingredient and the particular therapeutic effect to be achieved, and (b) the limitations inherent in the art of compounding such an active ingredient for therapeutic use in vitro, as well as in vivo in humans and other animals.

Examples of suitable unit dosage forms in accord with this invention are tablets, capsules, pills, powder packets, granules, wafers, and the like, segregated multiples of any of the foregoing, as well as liquid solutions, emulsions and suspensions. Liquid compositions can be administered in usual manners such as subcutaneously, intraperitoneally, intramuscularly, intravenously perorally or the like.

The amount of active ingredient that is administered in vivo as an effective immunostimulating amount depends on the age and weight of the patient, the particular condition to be treated, the frequency of administration, and the route of administration. The total daily dose range can be about 0.01 to about 400 milligrams per kilogram of body weight, more preferably about 0.1 to about 400 milligrams per kilogram of body weight. The human adult dose is in the range of about 70 to about 7000 milligrams daily, given either as a single dose or in 3 or 4 divided doses. Veterinary dosages correspond to human dosages with the amounts administered being in proportion to the weight and metabolic rate of the animal as compared to adult humans.

It will be appreciated by those skilled in the art that useful in vivo concentrations can vary from animal species to animal species. Those skilled workers also know that appropriate concentrations can be readily determined.

Concentrations for the in vitro contacting of animal cells are about $1 \times 10^{-6}$ molar to about $10^{-3}$ molar for cell concentrations of about $10^6$-$10^7$ cells per milliliter. More preferably, the concentration is about $1 \times 10^{-5}$ molar to about $3 \times 10^{-4}$ molar. The peak concentration; e.g., the concentration that provides the greatest adjuvanticity, mitogenicity or NK cell activation, for a given substituted guanine can vary as much as ten or more fold when studied in mouse as compared to human lymphocyte systems.

A composition can be solid or liquid. Physiologically tolerable carriers are well known in the art. Exemplary of liquid carriers are sterile aqueous solutions that contain no materials in addition to the active ingredient guanine derivative and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. The latter carriers are exemplified by Ringer's Injection, Dextrose Injection, Dextrose and Sodium Chloride Injection and Lactated Ringer's Injection. Preferably, the solution should be isotonic unless it is an oral pediatric suspension.

Liquid compositions can also contain liquid phases in addition to and to the exclusion of water. Exemplary of such additional phases are glycerin, vegetable oils, such as sesame oil, cotton seed oil, and water-oil emulsions.

Exemplary solid carriers include those materials usually used in the manufacture of pills, tablets or capsules, and include corn starch, lactose, dicalcium phosphate, thickeners such as tragacanth gum and methylcellulose U.S.P., finely divided $SiO_2$, polyvinylpyrrolidone, magnesium stearate and the like. Additionally, the solid carrier can include biodegradable and non-biodegradable polymers, polypeptide carriers, affinity carriers such as AFFI-GEL 601 (phenyl boronate resin available from BIO-RAD Laboratories, Richmond, California), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide aspartic-phenylalanine methyl ester sweetener sold under the trade name NUTRASWEET ® (aspartame) by G. D. Searle Co.

C. Processes of Treatment

A process for enhancing the immune responses of leukocytes is also contemplated. Preferably, the immune response is an antigen-specific response. In accordance with this method, leukocytes such as lymphocyte preparations, B cells, T cells, NK cells, LAK cells, neurophils and macrophages are contacted separately or in combination in an aqueous medium with a before-described composition containing an immunostimulating effective amount of a before-described guanine nucleoside derivative.

The process can be practiced in vivo in humans, laboratory mammals such as mice, rats and guinea pigs or in veterinary animals and pets such as pigs, horses, cattle, dogs and cats. The process can also be practiced in vivo in cell cultures such as in hybridoma culture for the production of monoclonal antibodies.

The leukocytes are contacted in an aqueous medium regardless of whether the composition of substituted guanine derivative is itself a solid or liquid, or whether or not the liquid of the composition is aqueous. For the in vivo process, the aqueous medium is supplied at least in part by the water of the blood or lymph. For in vitro process, the aqueous medium is supplied at least in part by the culture medium used.

Contact between the composition and leukocytes is maintained for a time period sufficient for the contacted cells to manifest the enhancement of their immune response. The immunostimulation can itself be manifest in cellular proliferation, enhanced antibody secretion, enhanced T helper activity, enhanced cytotoxic activity, enhanced cytokine production from T cells, B cells, NK cells and macrophages, enzyme secretion from neutrophils, and the like, as are well known.

The specific results discussed hereinafter illustrate a non-specific mitogenic response of murine spleen B cells, as well as the preferred NK cell-mediated cytotoxicity and antigen-specific antibody responses of murine B cells that can, but need not be, depleted of T suppressor cells. Additional illustrative antigen-specific immunoenhancements that can be achieved using a process of the invention include proliferation of T cells, the in vitro reconstitution of the primary and anamestic immune responses in murine or human immunodeficient B cells, T cell-replacing activity in normal or immunodeficient murine or human B cells, and an in vivo enhancement of murine antibody production.

For use in vivo, contact between leukocytes and a composition is typically maintained for a time period sufficient for the animal to clear the guanine derivative from its body as by metabolism, excretion or both processes. That time period can be longer than that required for immunostimulation to be manifest. Contact with an individual unit dose is typically maintained for a time period of hours to about a week or more, depending, for a given compound, upon the carrier or vehicle used.

Contact in vitro can be maintained for a period of time sufficient for one of the before-described immunostimulations to become manifest as determined by standard assay techniques. Such maintenance times typically take about one to about seven days of time, and more usually about 2 to about 6 days.

A contemplated compound was assayed to determine its ability to enhance the immune response. The assays carried out are described hereinafter. In each of the assays, 7-allyl-8-oxoguanosine (loxoribine) was used as a standard. The results of each of the assays are reported in Table 2 that follows the description of the assays.

NK ASSAY

A. Animals

Male CBA/J and C3H/HeJ mice were obtained from Jackson Laboratories, Bar Harbor, Me. All mice were used at 8 to 12 weeks of age. They were fed Purina rodent laboratory chow and tap water ad libitum.

B. Tissue Culture Medium

Culture medium was RPMI 1640 medium (flow Laboratories, McLean, Va.) supplemented with 5 percent fetal bovine serum (FBS, GIBCO, Grand Island, N.Y. or HyClone Laboratories, Logan, Utah) and 100 IU/ml penicillin, 100 µg/ml streptomycin, 2 mM L-glutamine (all from Flow Laboratories, McLean, Va.).

C. Cell Lines

The NK-sensitive cell line YAC-1, was originally obtained from Dr. John Roder, Mount Sinai Hospital, Toronto, Ontario. It was maintained in basic culture medium in a 37° C., 5 percent $CO_2$ incubator. Cell lines were tested periodically for mycoplasma and found to be negative.

D. Loxoribine (7-allyl-8-oxoguanosine)

For these in vitro experiments 10.2 mg, loxoribine (provided by the R. W. Johnson Pharmaceutical Research Institute) were dissolved in 0.1 ml 1N NaOH. This was further diluted with 9.9 ml culture medium to provide a 3 mM stock solution. The stock solution was filtered through 0.22 mM millipore filters and diluted further with sterile medium. Vehicle controls contained equivalent concentrations of NaOH.

E. Lymphoid Cell Preparation

Mice were killed by cervical dislocation and spleens were removed aseptically and pressed through a stainless steel mesh. Cells were centrifuged for 10 minutes at 220Xg and resuspended in culture medium at $10^7$ cells/ml.

F. In Vitro Culture of Lymphoid Cells with Loxoribine

Spleen cells at 4 concentrations, each in triplicate ($10^6$, $5 \times 10^5$, $2.5 \times 10^5$, $1.25 \times 10^5$ spleen cells) were cultured in 96 well, round bottom culture trays (Linbro, Flow Laboratories, McLean, Va.) in a volume of 100 µl. Compounds were added to the wells in a volume of 100 µl to give appropriate final concentrations such as 3, 10, 30, 100, 300 µM of drug. Cultures were incubated for 18 hours at 37° C. in 5 percent $CO_2$.

G. $^{51}$Chromium Release Assay

YAC-1 target cells ($5 \times 10^5$) were incubated with 100 µCi sodium $^{51}$Cr (Amersham Canada, Oakville, Ontario) for 1 hour at 37° C., in 5 percent $CO_2$, washed three times with Phosphate Buffered Saline (PBS), and suspended in culture medium at $5 \times 10^4$/ml. The plates containing cells to be assayed for cytotoxic activity were centrifuged at 220Xg for 10 minutes, 100 µl supernatant were removed from each well, and 100 µl target cells were added to the wells. The plates were centrifuged for 5 minutes at 150Xg, incubated at 37° C. in 5 percent $CO_2$ for 4 hours, and centrifuged for 5 minutes at 300Xg. Supernatants were removed from the wells using the Skatron Supernatant Collection System (Skatron, Sterling, Va.) and the samples were counted in a Beckman gamma counter. Maximum lysis was obtained by counting the total CPM in $5 \times 10^3$ target cells. Minimum release, obtained from target cells cultured with medium alone, was always lower than 10 percent of the maximum CPM. Percent Lysis was calculated as:

$$\frac{\text{Sample CPM} - \text{Minimum CPM}}{\text{Maximum CPM} - \text{Minimum CPM}} \times 100$$

Each time a compound was assayed, loxoribine was assayed as well for direct comparison purposes. The $ED_{50}$ value, taken as a measure of potency, varied from 15–34 $\mu M$ for loxoribine (see Table 2). The maximal response for loxoribine was assigned the value of 100 percent. The activity for other compounds is given in Table 2 as a direct comparison to that of loxoribine.

MURINE ADJUVANTICITY

In Vitro Adjuvanticity

Contacting animal antibody-producing cells with a composition useful herein provides an adjuvant effect on the primary antibody response to SRBC (sheep red blood cells) and other immunogens when evaluated in vitro. The immune response-stimulating composition and effective amount of immunogen, SRBC, are typically admixed to contact the cells substantially simultaneously. The words "antigen" and "immunogen" are used interchangeably here.

At optimal concentration, a composition containing an effective amount of a useful substituted guanine derivative enhances the response to antigen by at least about 4–25-fold. The effect is dose dependent. Enhancement of the antibody response cannot be accounted for by the additive effects of the specific response to antigen and the polyclonal response to the substituted guanine derivative.

The adjuvant effect of compositions containing a useful substituted guanine derivative is exerted on immunogen-experienced (primed) as well as on naive cells. Both responses are enhanced by contacting the cells with compositions containing an effective amount of substituted guanine derivative. This adjuvant effect is dependent upon the concentration of immunogen added to culture. Thus, the primary IgM as well as the secondary IgM and IgG responses to immunogen (antigen) are augmented by contacting B cells with a composition containing an effective amount of a substituted guanine derivative as active ingredient, and maintaining that contact as discussed herein.

Whereas immune responses; i.e., responses of B lymphocytes (or B cells) are observed to be enhanced at all immunologically effective doses of immunogen administered in an appropriately supportive cellular milieu, the degree of enhancement is usually greatest at optimal or near optimal immunogen concentrations. Additionally, adjuvanticity of substituted guanine derivatives is synergistic with immunogen and not just simply due to the sum of independent immunogen-specific and polyclonal (nonspecific) responses, as described above for primary antibody responses.

In summary, an enhanced immune response can thus be obtained by contacting B cells substantially simultaneously with an effective, priming amount of immunogen and an immune response-enhancing composition useful herein, followed, after a primary immune response is obtained, by an additional contacting of the primed cells with a further effective amount of immunogen (antigen) alone or substantially simultaneously with a further amount of immune response-enhancing composition.

Substituted guanine derivative-containing compositions useful herein are thought to enhance the primary humoral immune response by acting directly upon the B cell and/or the immunogen-presenting cell. Thus, one of these derivatives enhances the antibody response mounted against T-independent antigens; i.e., responses that involve B cells and immunogen-presenting cells. In addition, compositions containing a substituted guanine derivative can replace the need of B cells for T helper cells, as discussed hereinafter, and therefore exert their adjuvant effect in cultures initiated in the substantial absence of intact, functional T cells. A replacement of T cells with T cell helper activity contained in mixed lymphocyte culture (MLC) supernates or other lymphokines that can be derived from T cell does not diminish the ability of a substituted guanine derivative to augment the antibody response.

Still further, the synergy observed between the soluble T cell signal contained in MLC supernate and the substituted guanine derivative-containing composition acting on antigen-stimulated B cells indicates that the signal supplied by each is qualitatively distinct. This synergy is observed over a range of supernate concentrations, indicating that the substituted guanine derivative is not simply providing more of the same "signal" that T cells provide. A comparable degree of synergy can be observed when such B cell cultures are supplemented with T cells rather than with T cell-like supernates (which are in fact T cell derived), and are contacted in the presence of immunogen with a substituted guanine derivative-containing composition useful in this invention.

In summary, T cell-mediated effects of the adjuvanticity of substituted guanine derivatives are not ruled out by the observation of T-independence for that adjuvanticity, i.e., the existence of a T cell-independent phase. Thus, more substantial enhancement can be observed from a composition containing the substituted guanine derivative under conditions of stimulation with T-dependent and T-independent type 2 antigens (T cell dependent situations) than with T-independent type 1 antigens (more completely T cell-independent), which suggests the presence of a T cell-dependent component. Moreover, substituted guanine derivatives are thought to act (either directly or indirectly) on precursors of T helper cells to increase the ability of a population of such cells to support (i.e., help) an antibody response to immunogen.

Lymphocyte cultures

The serum-containing culture medium was prepared to contain the following per 100 milliliters: 91.9 milliliters RPMI 1640 (Flow Laboratories, Inc., Rockville, Md.), 0.1 milliliters of $100 \times$ glutamine, 1.0 milliliter of $100 \times$ sodium pyruvate, 1.0 milliliter of $50 \times$ nonessential amino acids, 1.0 milliliter of water containing $10^4$ units of penicillin G and $10^4$ micrograms of streptomycin, and 5.0 milliliters of a supportive lot of fetal calf serum (FCS). These ingredients were admixed to apparent homogeneity. Spleen cell suspensions and populations enriched for splenic B cells were prepared as described in Goodman et al., *J. Immunol.*, 12:1905 (1978).

For evaluation of the primary humoral immune response to sheep erythrocytes (SRBC), $5 \times 10^6$ to $10^7$ murine spleen cells were cultured in 1.0 milliliter of 5 percent FCS-containing medium for 4 or 5 days in the presence and absence of immunogen. Cells were incubated in culture trays (Costar, Cambridge, Mass.) at 37° C., in a humidified atmosphere of 10 percent $CO_2$ in air using tissue culture boxes (CBS Scientific, Del Mar, Calif.) that were rocked at a frequency of 7 cycles per minute. Pooled SRBC are available from the Colorado Serum Co., Denver, Colo.

Mice

CBA/CaJ mice, 8-16 weeks of age, are purchased from the Jackson Laboratory, Bar Harbor, Me. A breeding nucleus of CBA/N mice was provided by the Animal Production Section, National Institutes of Health, Bethesda, Md. SJL, BDF$_1$ and C57BL/6J mice 8-16 weeks old were obtained from the mouse breeding facility at Scripps Clinic and Research Foundation, La Jolla, Calif. All mice were maintained on Wayne Blox F6 pellets (Allied Mills, Inc., Chicago, Ill.) and chlorinated water acidified with HCl to a pH value of 3.0

Cell Preparations

Spleen and thymus cell suspensions were prepared as described in Goodman et al., *J. Immunol.*, 121:1905 (1978). B cell-enriched populations were prepared by treating $10^8$ spleen cells with a 1:1000 dilution of monoclonal anti-Thy 1.2 antibody (New England Nuclear, Boston, Md.) for 30 minutes at 4° C. Treated cells were centrifuged at 280×gravity for 10 minutes, antibodies were removed, and the cells were resuspended in a 1:6 dilution of CBA RBC-absorbed guinea pig complement at 37° C. for 45 minutes. Cells were then washed and cultured as described before.

The mouse adjuvanticity assays using a contemplated substituted guanine derivative and similar control assays using loxoribine were carried out on the same days.

MITOGENESIS ASSAY

Lymphocyte cultures

Murine spleen cells were cultured in microculture plates (No. 3546, Costar, Cambridge, Mass.) at a cell density of $4\times10^6$ viable cells milliliter in a volume of 0.1 milliliter, together with incremental concentrations of assayed compounds. Microcultures were incubated at 37° C. in a humidified atmosphere of 5 percent $CO_2$ in air. Cultures were fed daily with 8 microliter of nutritional cocktail, Mishell and Dutton, *J. Exp. Med.*, 126:423 (1967).

Measurement of DNA synthesis. During the final 24 hours of culture, cells were radiolabeled with 1.0 micro Ci of [$^3$H]TdR/culture (5 Ci/mM, Amersham Radiochemicals, Amersham, England). The microcultures were harvested with a Brandel cell harvester, Model 200A (Cambridge Technology, Inc., Cambridge, Mass.) onto glass fiber filter strips. Filter disks were transferred to plastic scintillation vials, covered with liquid scintillation cocktail, and counted in a Beckman LS-230 liquid scintillation counter.

Because there is some variability between runs of the same compound, such as loxoribine, some of the data in Table 2 are presented as ranges of numbers where multiple experiments were conducted. The maximal response of loxoribine is represented by 100 percent, and the maximal response of the assayed compounds is given relative to that value. In addition, the ED50 values are given for loxoribine and the analogs listed as part of this invention.

TABLE 2

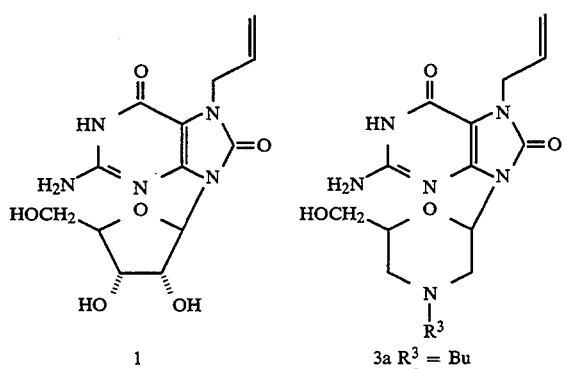

3a R$^3$ = Bu
3b R$^3$ = Ph$_2$CH

| Compound | NK Activation (Potency) | Mitogenicity | Murine Adjuvanticity |
|---|---|---|---|
| 1 Loxoribine (standard) | 100% (15-34 μM) | 100% (10-50 μM) | 100% (3-20 μM) |
| 3a | 94% (17 μM) | 52-96% (49-71 μM) | 38% (5 μM) |
| 3b | 46% (12 μM) | Not Tested | Not Tested |

As is apparent from the results reported in the table, Compound 3a is very potent in these assays.

The preparation of Compounds 3a and 3b reported in the table, will now be described in the following examples:

EXAMPLE 1

2-Amino-7-(2-propenyl)-9-[2-R-[4-butyl-6-S-(hydroxymethyl)-morpholino]]purine-6,8(1H)-dione Hydrate (Compound 3a)

A suspension of 7-allyl-8-oxoguanosine (2 g) in water (40 mL) was treated with NaIO$_4$ (1.52, 1.2 mol-equivalents) with cooling in an ice/water bath. This suspended sample went into solution over the period of several minutes. After 15 minutes, BuNH$_2$ was added (0.58 mL, 1 mol-equivalent) followed by immediate addition of HOAc (about 0.2 mL) to adjust the pH value in the range of 6-7. NaCNBH$_3$ (0.72 g) was added, resulting in considerable bubbling (the pH was still in the 6-7 range). After one hour, CHCl$_3$ was added to the solution along with saturated aqueous NaHCO$_3$. After extraction into CHCl$_3$ (3×), the organic layers were combined, dried (MgSO$_4$), filtered and concentrated. The residue was purified on silica gel (CH$_2$Cl$_2$/MeOH, 92:8) and by recrystallization (MeOH/Et$_2$O/pentane) to give a white solid that was dried at 70° C. overnight under vacuum (170 mg, 15 percent), m.p. 135°-150° C. (dec). IR (KBr) 3300-3500, 2940, 1688, 1640, 1600 cm$^{-1}$. [α]$_D^{25}$-18.6° (c 1.00 MeOH) MS (FAB) m/e 379 (M+1, 20 percent). 400-MHz $^1$H NMR (CDCl$_3$; key morpholine resonances only) δ2.18 (t, 1H, H2'-ax), 2.72 (t, 1H, H2'-eq or H4'-eq), 2.80 t,1H, H2'-eq or H4'-eq), 3.16 (t, 1H, H4'-ax), 5.68 (AB q, 1H, H1', J=1,9 Hz).

Anal. Calcd. for C$_{17}$H$_{26}$N$_6$O$_4$. 0.4H$_2$O: C, 52.95; H, 7.00; N, 21.79; H$_2$O, 1.87 Found: C, 52.74; H, 6.88; N, 21.47; H$_2$O, 1.50

EXAMPLE 2

2-Amino-7-(2-propenyl)-9-[2-R-[4-di(phenyl)methyl-6-S-(hydroxymethyl)-morpholino]]purine-6,8(1H)-dione (Compound 3b)

This compound was prepared in a similar manner as that described for the preparation of Compound 3a, except replacing butylamine with benzhydryl amine, to give Compound 3b (15 percent), recrystallized from MeOH/water (m.p. 273°–275° C.). $[\alpha]_D^{25}$-19.1° (c 0.47, MeOH/CHCl$_3$, 2:1). 400-MHz $^1$H NMR (DMSO-d$_6$ was the best solvent for sharp resolution) and MS data support the structure.

Anal. Calcd. for $C_{26}H_{28}N_6O_4 \cdot 0.2H_2O$: C, 63.45; H, 5.82; N, 17.08; H$_2$O, 0.73 Found: C, 63.37; H, 5.30; N, 16.93; H$_2$O, 0.68

The foregoing description and the examples are intended as illustrative and are not to be taken as limiting. Still other variations within the spirit and scope of this invention are possible and will readily present themselves to those skilled in the art.

What is claimed:

1. A compound of the formula I:

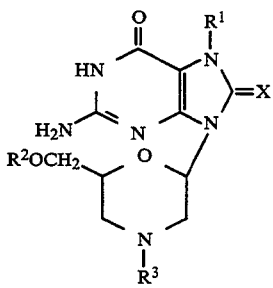

wherein X is O or S;

R$^1$ is a hydrocarbyl or substituted hydrocarbyl moiety having a length of about one to about seven carbon atoms;

R$^2$ is hydrogen or C$_1$–C$_8$ acyl;

R$^3$ is selected from the group consisting of hydrogen, C$_1$–C$_5$ aliphatic hydrocarbyl, aralkyl, and substituted aralkyl groups; and the pharmaceutically acceptable base addition salts thereof.

2. The compound of claim 1 wherein R$^1$ is selected from the group consisting of (i) a C$_1$–C$_5$ aliphatic hydrocarbyl group, (ii) an aralkyl hydrocarbyl radical and (iii) a substituted aralkyl radical whose substituent is selected from the group consisting of halogen, nitro, C$_1$–C$_2$ alkyl, trifluoromethyl, amino and substituted amino, wherein the amine substituents are mono- or di-C$_1$–C$_2$ alkyl, C$_1$–C$_3$ acyl and sulfonyl groups.

3. The compound of claim 1 wherein R$^2$ is hydrogen.

4. The compound of claim 1, wherein X is O.

5. The compound of claim 2 wherein R$^1$ is a C$_1$–C$_5$ aliphatic hydrocarbyl group.

6. A compound represented by formula I

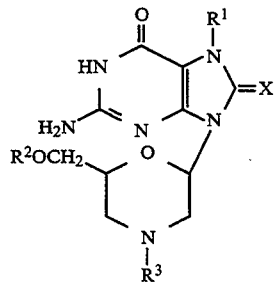

wherein X is O or S;

R$^1$ is a C$_1$–C$_5$ aliphatic hydrocarbyl group;

R$^2$ is hydrogen or C$_1$–C$_8$ acyl;

R$^3$ is selected from the group consisting of hydrogen, C$_1$–C$_5$ aliphatic hydrocarbyl, aralkyl, and substituted aralkyl groups; and the pharmaceutically acceptable base addition salts thereof.

7. The compound of claim 6 represented by formula II

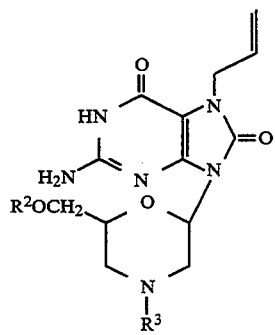

8. The compound of claim 7 wherein R$^2$ is hydrogen.

9. The compound of claim 8 wherein R$^3$ is a butyl group.

10. The compound of claim 8 wherein R$^3$ is a benzhydryl group.

11. A composition comprising a diluent amount of a physiologically acceptable carrier admixed with an immunostimulating effective amount of a compound of claim 1.

* * * * *